(12) United States Patent
Markle (10) Patent No.: US 12,392,696 B2
(45) Date of Patent: Aug. 19, 2025

(54) GAS PHASE STANDARD PREPARATION DEVICE AND METHOD OF USE

(71) Applicant: Doug Markle, Cumming, GA (US)

(72) Inventor: Doug Markle, Cumming, GA (US)

( * ) Notice: Subject to any disclaimer, the term of this patent is extended or adjusted under 35 U.S.C. 154(b) by 713 days.

(21) Appl. No.: 17/839,434

(22) Filed: Jun. 13, 2022

(65) Prior Publication Data

US 2022/0307954 A1 Sep. 29, 2022

Related U.S. Application Data

(63) Continuation-in-part of application No. 15/999,506, filed on Aug. 20, 2018, now Pat. No. 11,360,066.

(51) Int. Cl.
 *G01N 1/44* (2006.01)
(52) U.S. Cl.
 CPC ...................................... *G01N 1/44* (2013.01)
(58) Field of Classification Search
 None
 See application file for complete search history.

(56) References Cited

U.S. PATENT DOCUMENTS

| | | | | |
|---|---|---|---|---|
| 1,097,580 A | * | 5/1914 | Barclay | B41J 1/32 400/330 |
| 3,760,773 A | | 9/1973 | Christensen | |
| 4,036,915 A | | 7/1977 | Lucero et al. | |
| 4,142,860 A | | 3/1979 | Mayeaux | |
| 4,589,540 A | * | 5/1986 | Kampf | G01N 35/04 198/346.2 |
| 5,457,983 A | | 10/1995 | Sauvageau et al. | |
| 5,650,560 A | | 7/1997 | Troost | |

(Continued)

FOREIGN PATENT DOCUMENTS

| | | |
|---|---|---|
| EP | 500938 A1 | 9/1992 |
| WO | 2010072581 A1 | 7/2010 |
| WO | 2017180933 A1 | 10/2017 |

OTHER PUBLICATIONS

Platonov, I. A. et al. "Methods and Devices for the Preparation of Standard Gas Mixtures." Journal of Analytical Chemistry (New York, N.Y.) 73.2 (2018): 109-127. Web. (Year: 2018).

(Continued)

*Primary Examiner* — Benjamin R Whatley
*Assistant Examiner* — Curtis A Thompson
(74) *Attorney, Agent, or Firm* — Lippes Mathias LLP; Mitchell Ghaneie; Josephine Chen (57) ABSTRACT

A gas phase standard preparation device and method of use for creating a final reference material is disclosed. The final reference material is used to quantitate certain gaseous compounds in collected air samples. This is accomplished by providing a sealed ampule tube with an ampule containing reference material that is eventually breached by the gas preparation device. Once the ampule is breached, the reference material within the ampule is blended with a diluent gas and forced into a reference material cylinder. The concentration of the final reference material within the reference material cylinder can then be verified for use in testing collected air samples. Accordingly, this device allows for creating a custom final reference material onsite in a laboratory without the need for shipping in pre-made compressed gas cylinders for air quality testing.

19 Claims, 11 Drawing Sheets

(56) References Cited

U.S. PATENT DOCUMENTS

| | | |
|---|---|---|
| 6,234,001 B1 | 5/2001 | Sorensen et al. |
| 11,806,711 B1* | 11/2023 | Friedman ................ B01L 3/505 |
| 2002/0014275 A1* | 2/2002 | Blatt ..................... F17C 13/026 |
| | | 137/209 |
| 2017/0259268 A1* | 9/2017 | Wright ................ B01L 3/50273 |
| 2018/0021466 A1 | 1/2018 | Shomali et al. |
| 2020/0057040 A1* | 2/2020 | Markle .................. G01N 30/74 |

OTHER PUBLICATIONS

Barratt, R. S. "The Preparation of Standard Gas Mixtures. A Review." Analyst (London) 106.1265 (Aug. 1981): 817-. Web. (Year: 1981).

\* cited by examiner

GAS PHASE STANDARD PREPARATION DEVICE AND METHOD OF USE

CROSS-REFERENCE TO RELATED APPLICATIONS

This application is a continuation-in-part of U.S. non-provisional application Ser. No. 15/999,506, filed Aug. 20, 2018, the contents of which are incorporated by reference herein.

BACKGROUND OF THE INVENTION

A reference material or a certified reference material may be prepared for use for identifying and quantifying certain gaseous compounds in collected air samples. Commercial companies (such as Linde, Inc. and Airgas, Inc.) and National Institute of Standards and Technology (NIST) provide premade standardized compounds, also known generally as "reference materials" or "certified reference materials," that are used for comparison with an air sample. In the art and hereinafter, the phrase "Reference Materials" may be used to refer generally to either or both of "uncertified" reference materials or certified reference materials. Once the air sample is compared to the Reference Material, the tested-for volatile compounds are then quantitated accordingly. However, the current system for providing standardized testing in laboratories becomes problematic when a lab requires a different concentration than those provided by Air Gas, Linde, NIST, or other commercial company. Additionally, the current system requires shipment of high-pressure cylinders which requires special shipping methods. In the current system, when the pressurized cylinders have reached their expiration date, they either need to be shipped back to the supplier for recertification or disposed of, both of which creates complications for laboratories. In other words, as technology advances and labs require different concentrations of Reference Materials, the invention described and claimed herein allows such labs to create a desired reference material at the desired concentration onsite and avoid the complications of sending and receiving certified pressurized cylinders.

BRIEF SUMMARY OF THE INVENTION

The gas phase standard preparation device described herein allows laboratories to request a custom reference material or a custom certified reference material for the requested air quality analysis. This is accomplished by providing a premade sealed ampule that contains the requested ampule reference material, which is comprised of a chemical cocktail at a pre-determined concentration. The ampule containing the ampule reference material is then placed into a steel sleeve and the sleeve is sealed. The sleeve is then placed into a gas phase standard preparation station, which may include separate compartments.

In one embodiment a gas phase standard preparation device includes a housing frame, a sealed ampule tube, a gas/vacuum supply line, a pressure sensor, a vacuum pump valve, a diluent gas valve, a crusher assembly, and an electronics control board. The sealed ampule tube further includes an ampule, an ampule sleeve, a first connector and a second connector. The ampule sleeve has a first end and a second end. The gas/vacuum supply line has a first end and a second end, wherein the first end of the gas/vacuum supply line is connected to the pressure sensor and the second end of the gas/vacuum supply line is connected to the first end of the ampule sleeve. The vacuum pump valve and the diluent gas valve are fluidly coupled to the pressure sensor. The crusher assembly is configured to provide a uniform deformation of the ampule sleeve, thereby causing a breaching of the ampule. The electronics control board electronically couples to the crusher assembly, pressure sensor, the vacuum pump valve, and the diluent gas valve. The second end of the ampule sleeve is fluidly coupled to a reference material cylinder.

In one embodiment a method of using the gas phase preparation device described above further includes placing a clean and evacuated reference material cylinder into the housing frame, connecting the first end of the ampule sleeve to the gas/vacuum supply line, connecting the second end of the ampule sleeve to the reference material cylinder, evacuating the ampule sleeve, leak-checking the ampule sleeve, opening a shutoff valve of the reference material cylinder, starting a trickle flow of a diluent gas into the gas phase standard preparation device, energizing a motor of the crusher assembly to provide linear movement of a carriage to provide a breaching of the ampule, breaching the ampule and releasing ampules reference material, and starting a preparation program. The preparation program includes filling the reference material cylinder with the diluent gas and the ampule reference material, thereby forming a final reference material, and closing the shutoff valve of the reference material cylinder. The method may further include verifying the concentration of the final reference material within the reference material cylinder.

NUMBER REFERENCES

5—Sealed ampule tube
10—Ampule
15—Ampule sleeve
20—Spacers
25—Connectors
40—Reference material cylinder
42—Shutoff valve 50—Preparation Station (First Embodiment)
50A—Housing
51—First lid
52—Second Lid
53—Clasp
54—Hinge
55—Vacuum pump
56—Vacuum pump valve
60—Diluent gas cylinder
61—Diluent gas valve
64—Tube
65—Pressure sensor
66—gas/vacuum supply line
70—Mandrel
75—Lid Mandrel
80—Electronics control board
82—Power Source
83—AC Mains
84—Battery
85—Insulation wall
87—Bulkhead
90—Heat sink
100—Preparation Station (Second embodiment)
100A—Housing
105—Bearing
110—Load sensor
115—IR Sensor
120—Formed adapter
122—Fulcrum point protrusion
200—Preparation Station (Third embodiment)
202—Housing frame
203—Shroud compartment
204—Crusher assembly
205—Support brace
206—Motor
207—Motor power source
208—Electronics support wall
210—Drive assembly
218—Lower support bracket
220—Screw shaft
228—Guide tracks
230—Carriage
231—Fasteners
232—U-brace
233—Support arms
234—Nut bracket
235—Slides
236—Clamping assembly
237—Crusher wheel
238—Crusher wheel assembly
239—Wheel mountings
240—Clamp brackets
250—Upper support bracket
260—Mandrel base

LETTER REFERENCES

A—Longitudinal central axis of crusher wheel 237
B—Longitudinal central ampule mounting axis of mandrel base 260
C—Vertical axis of support arms 233

DETAILED DESCRIPTION OF THE EMBODIMENTS

This device and method of use for a gas phase standard preparation device (the "Device") allows for the Reference Material to be created in a laboratory instead of ordering premade, high-pressure cylinders that are to be utilized in the lab or at an off-site location. This Device additionally allows for the Reference Material to be tailored or customized for the lab that it is to be used in. This is beneficial when the companies or the National Institute of Standards and Technology (NIST) that produce such reference materials are incapable of providing a premade standardized reference material. This is also beneficial for the laboratory and the environment as this Device may contribute to the reduction of waste cylinders because the high-pressure cylinders may be reused. This Device would also result in drastically lower shipping costs due to the fact that a sealed ampule would be shipped as compared to a premade, high-pressure cylinder.

Figure 1:
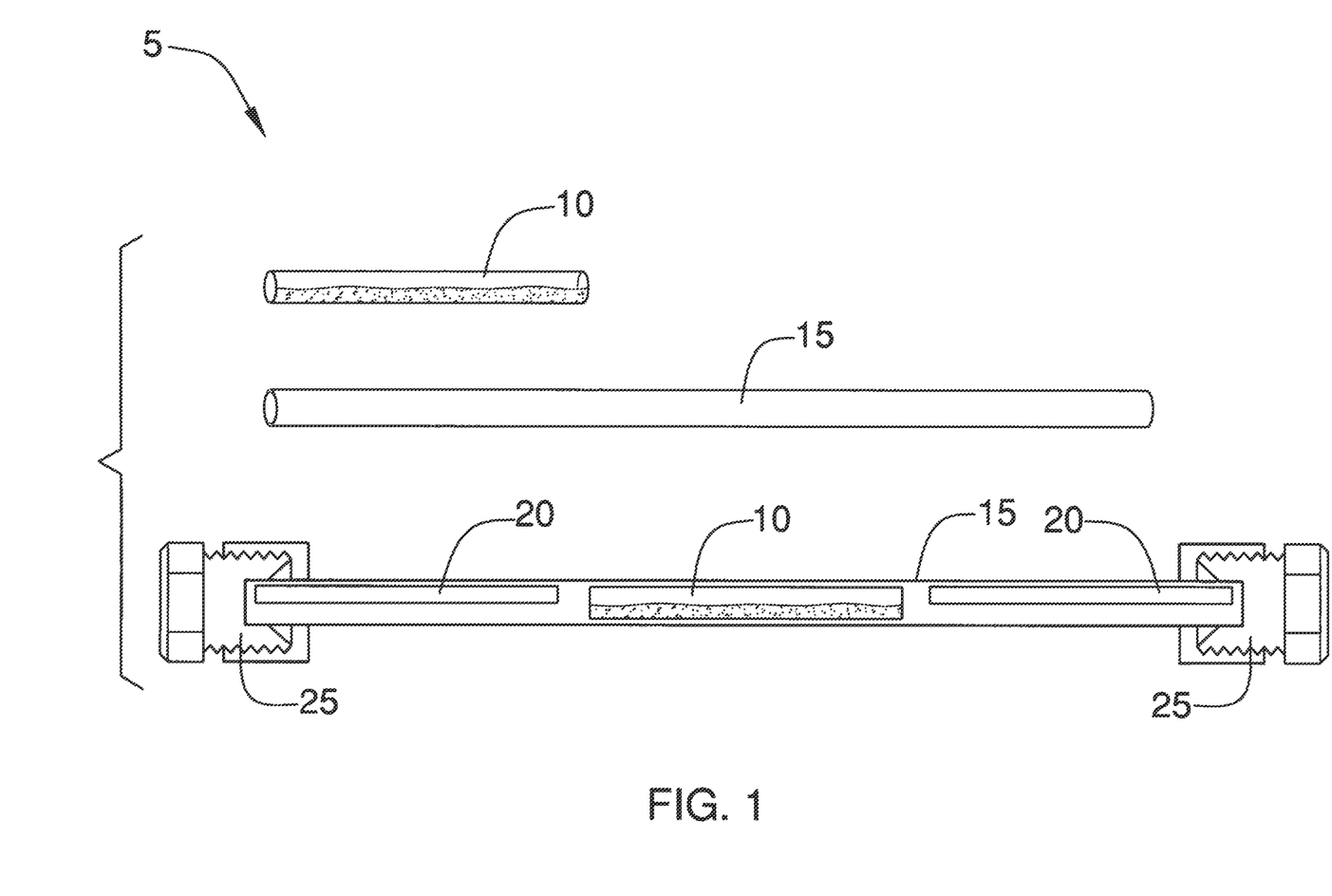
FIG. 1 shows the ampule sealed within the ampule sleeve prior to being placed into the gas phase standard preparation station.

As shown in FIG. 1, a sealed ampule tube 5 includes an ampule 10, an ampule sleeve 15, and connectors 25. Although connectors 25 are shown as compression fittings (with plugs), they may be any suitable connector utilized for joining piping or tubing and which is configured to provide airtightness and compatibility. The ampule 10 may be formed as a glass sealed tube and the tube may undergo Non-Destructive Testing (NDT) to meet certain quality standards. The ampule 10 contains a mixture of chemicals at predetermined concentrations, which collectively are referred to as ampule reference material. This ampule reference material will be blended with diluent gas to form a final reference material which will be verified for concentration. The ampule 10 is placed within the ampule sleeve 15. The ampule sleeve 15 should be made of airtight and inert or passivated materials. This can be accomplished by providing a stainless-steel sleeve that is internally coated with a passivation material such as a silica ceramic. The ampule sleeve 15 includes a first end and a second end with each end having a connector 25, which can be seen in FIG. 1. While the ampule 10 is typically made of glass, it may be made of any suitable material compatible with the intended chemicals and pressures. It is anticipated that the sealed ampule tube 5 may also include one or more spacers 20 for maintaining the ampule 10 in a specific location within the ampule sleeve 15.

The ampule sleeve 15, which contains the ampule 10, is placed within a preparation station. The preparation station is described herein as various embodiments: a first embodiment for preparation station 50, a second embodiment for preparation station 100, and a third embodiment for preparation station 200.

First Embodiment

Figures 2A, 2B:
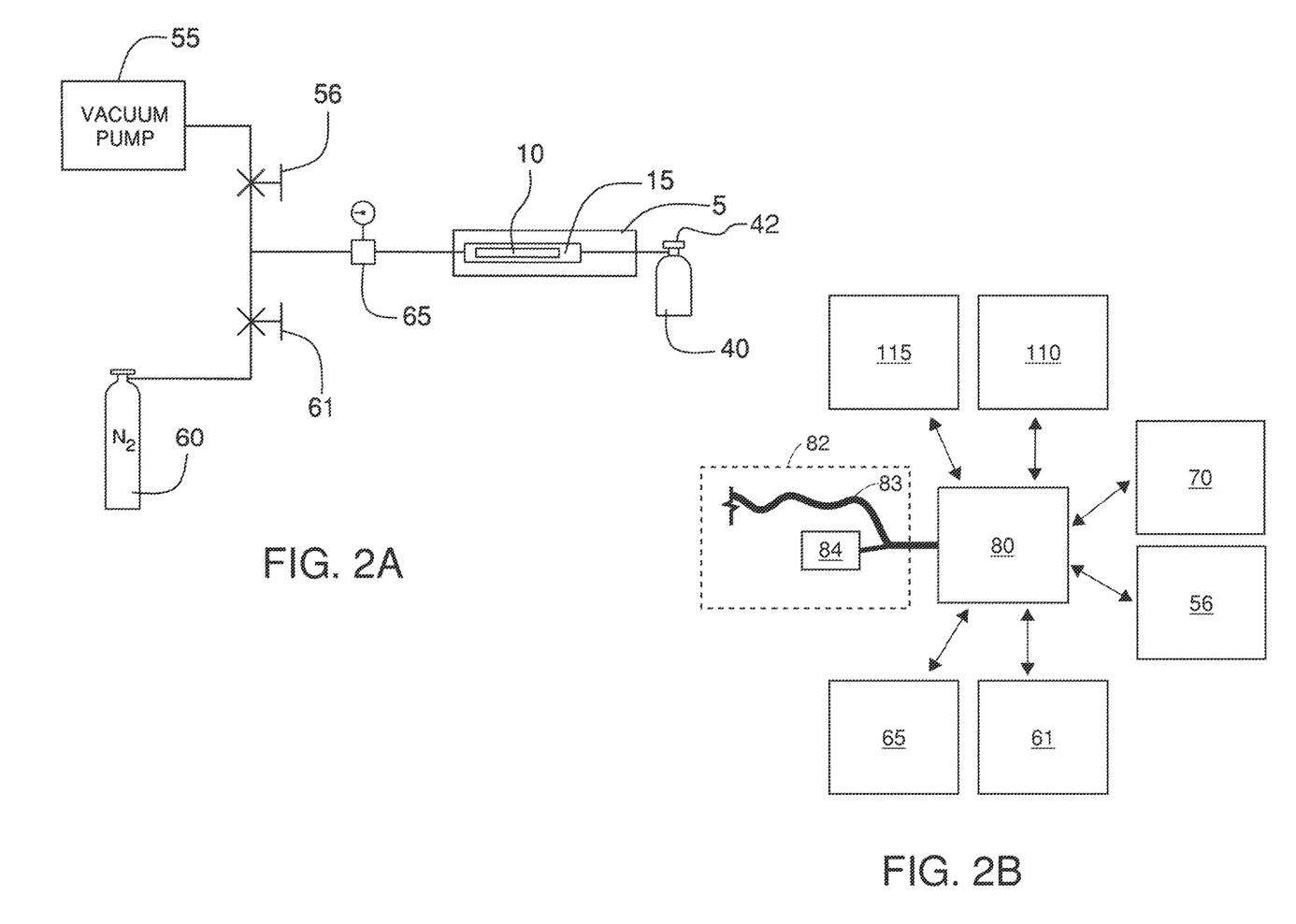
FIG. 2A is a schematic diagram of the preparation station.
FIG. 2B is a schematic diagram of the electric/electronic components of the preparation station.
Figure 3:
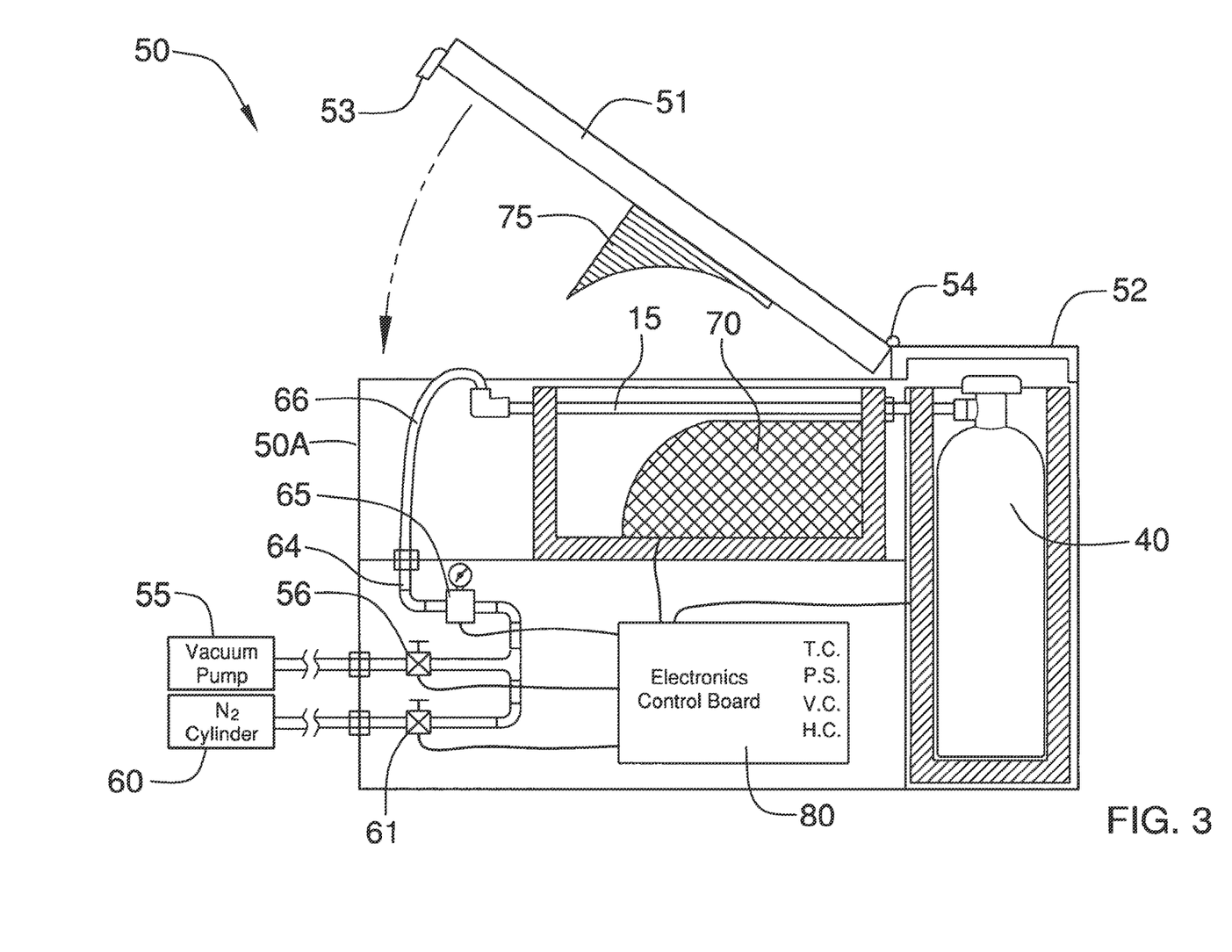
FIG. 3 shows a first non-limiting embodiment of the preparation station with the first lid in an open position.
Figure 4:
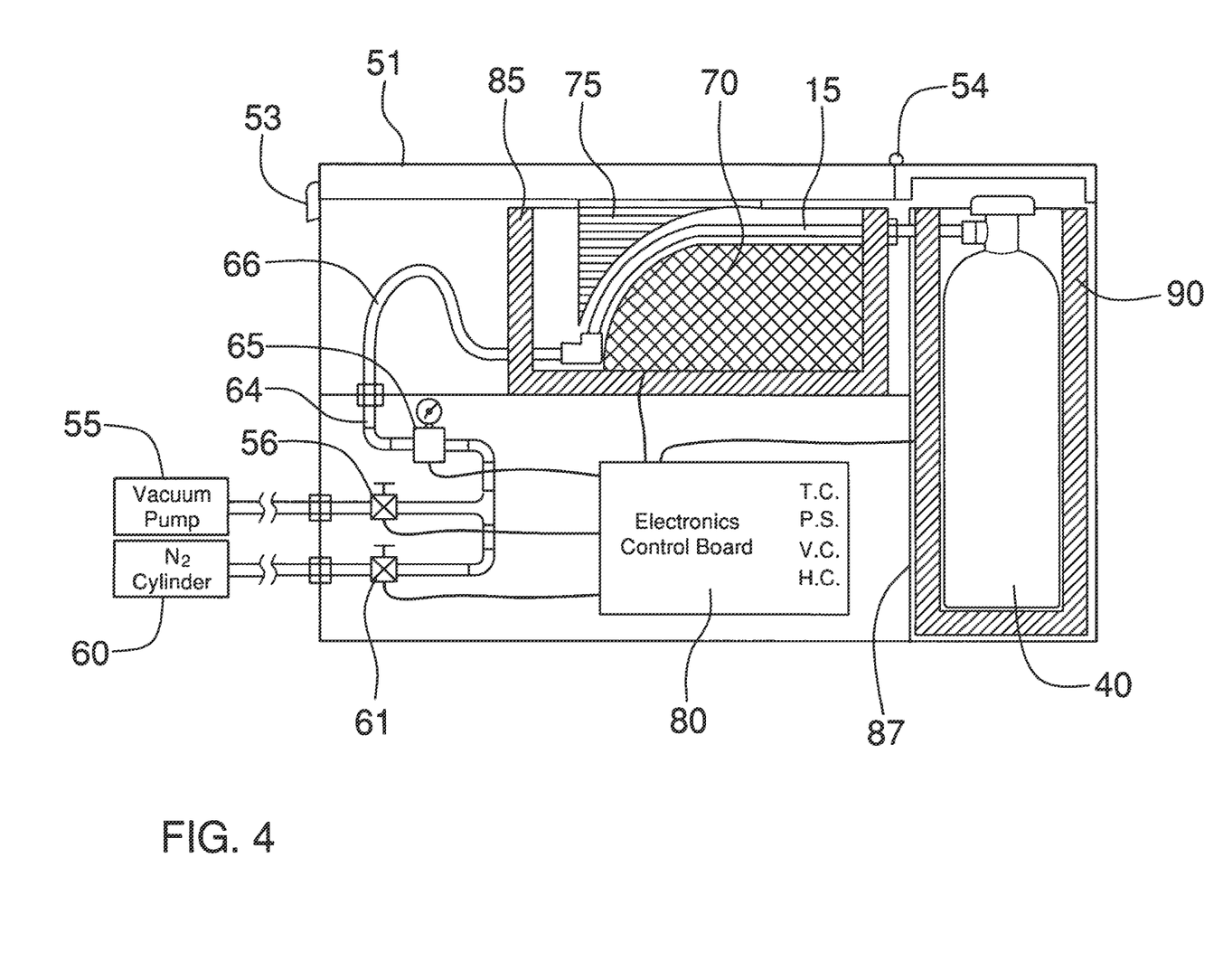
FIG. 4 shows the first non-limiting embodiment of the preparation station with the first lid in a closed position.

The first non-limiting embodiment for a preparation station 50 includes a housing 50A, sealed ampule tube 5, a first lid 51 with a clasp 53, a second lid 52, and a hinge 54 that the first lid 51 and second lid 52 are attached to and may pivot about, a heated mandrel 70, a lid mandrel 75, and an electronics control board 80. The electronics control board 80 of the gas phase standard preparation device is coupled to a power source 82, such as AC (alternating current) mains 83 or a battery 84 (see FIG. 2B). This embodiment further includes a load sensor 110, an IR sensor 115, and a formed adapter 120. Although, the first embodiment for preparation station 50 is shown and described as having four separate compartments, it is anticipated that the location, number, and orientation of the compartments may be altered without departing from the novel aspects of this non-limiting embodiment and the other non-limiting embodiments being claimed and described herein.

The first compartment includes a first connection and a second connection in the exterior side of the housing for coupling a vacuum pump 55 and diluent gas cylinder 60, respectively. Diluent gas cylinder 60 contains a suitable diluent gas, such as nitrogen gas, zero air, argon gas, or helium gas. The vacuum pump 55 is fluidly coupled to a vacuum pump valve 56 and the diluent gas cylinder 60 is fluidly coupled to a diluent gas valve 61. A set of tubes extend from the vacuum pump valve 56 and the diluent gas valve 61 and converge into a tube 64 as seen in FIG. 3 and FIG. 4. The vacuum pump valve 56 and the diluent gas valve 61 are each preferably proportional valves, but either may alternatively be comprised of a servo valve. The tube 64 connects to a pressure sensor 65. The tube 64 then extends from the pressure sensor 65 and fluidly couples to a gas vacuum supply line 66, which is provided in a second compartment as shown in FIG. 3 and FIG. 4.

The gas/vacuum supply line 66 is used to supply diluent gas to the ampule sleeve 15 of sealed ampule tube 5 and additionally to remove any room air from within the ampule sleeve of the sealed ampule tube prior to supplying the diluent gas. The gas/vacuum supply line 66 has a first end and a second end. The first end of the gas/vacuum supply line 66 is connected to the tube 64 and the second end of the gas/vacuum supply line 66 is connected to the first end of the ampule sleeve 15 which contains the ampule 10. It is anticipated that the gas/vacuum supply line 66 may be bendable or flexible.

The ampule sleeve 15 extends into a third compartment within the preparation station 50. The third compartment includes insulated walls 85 and the heated mandrel 70. The heated mandrel 70 provides heat at the location, or substantially at the location, of the ampule 10 within the ampule sleeve 15. The heated mandrel 70 is electrically coupled to and controlled by the electronics control board 80 in the first compartment. The second and third compartments within the preparation station 50 are adjacent to one another and are provided above the first compartment. The first lid 51 is provided above the second and third compartments, which is shown in FIG. 4. The first lid 51 provides access to the sealed ampule tube 5 for removal and installation.

The second end of the ampule sleeve 15 is connected to an evacuated reference material cylinder 40 with a formed adapter 120. The gas phase standard preparation device includes an interior bulkhead 87 attached to the housing that forms a fourth compartment. The reference material cylinder 40 is included in the fourth compartment, receives the Reference Material, and includes a shutoff valve 42. A heat sink 90 is included in the fourth compartments, which is accessible when the second lid 52 is opened. The heat sink 90 provides added containment security in the event that the integrity of the reference material cylinder 40 is compromised. The heat sink 90 also assists with absorbing heat as gas is compressed into the reference material cylinder 40. The insulation walls 85 are provided proximate to the heated mandrel 70, as shown in FIGS. 3-6, for conserving energy due to heat loss. When an individual desires to remove a reference material cylinder 40 or place a reference material cylinder 40 in the fourth compartment, the second lid 52 should be lifted.

A lid mandrel 75 is provided on the first lid 51. The lid mandrel 75 and heated mandrel 70 include arcuate surfaces, which are shown in FIG. 3 and FIG. 4. The arcuate surface of the lid mandrel 75 compliments the arcuate surface of the heated mandrel 70. Accordingly, when the sealed ampule tube 5 is installed, the arcuate surface of the lid mandrel 75 will bend the ampule 10 within the sealed ampule tube 5 against the heated mandrel 70, thereby breaking the ampule and releasing the ampule reference material within it.

The electronics control board 80 is electronically coupled to various electrical components within the gas standard preparation device as well as includes thermocouple control (T.C.), pressure sensor control (P.S.), valve control (V.C.), and heater control (H.C.). In this first non-limiting embodiment, the electronics control board 80 controls the IR sensor 115 thermocouple included in the compartment housing the reference material cylinder 40. The electronics control board 80 also controls the pressure sensor 65, the vacuum pump valve 56, the diluent gas valve 61, and the heater control which is connected to the heated mandrel 70. In addition, it is anticipated that the lid mandrel 75 may include heating elements and be electronically coupled to the electronics control board 80. The heating elements would be configured to heat the mandrel to a temperature of up to about 240 degrees maximum. The desired temperature would depend on what is needed for each application, which would depend on the compounds/chemicals contained within ampule 10. Electronics control board 80 is electronically coupled to with IR sensor 115 to allow for monitoring of the temperature of reference material cylinder 40 while being filled with gas, to prevent overheating, and with load sensor 110 for monitoring the weight of reference material cylinder 40 while it is being filled with gas, to determine the mass of gas being added.

Figure 7:
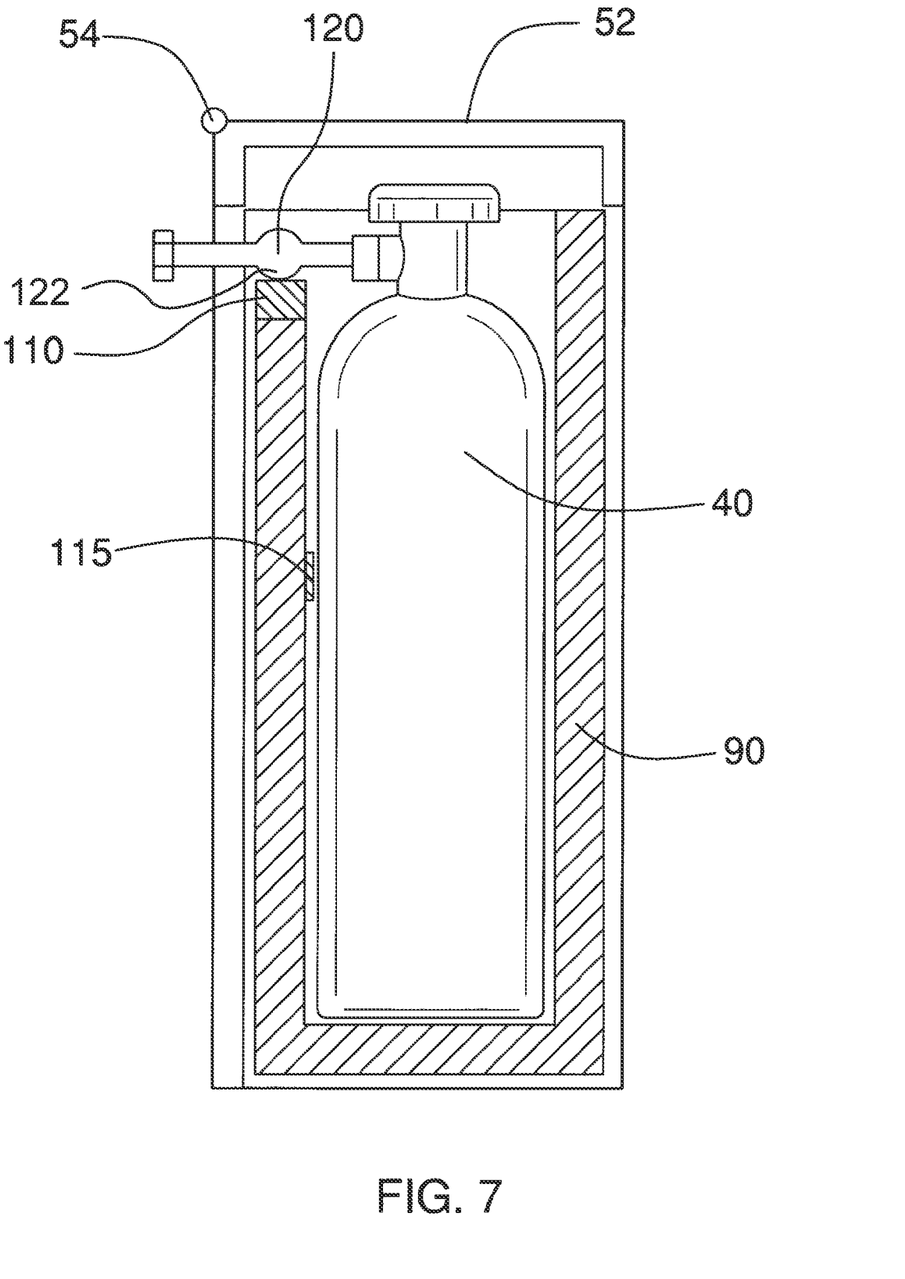
FIG. 7 shows the compartment of the first and second non-limiting embodiments holding the cylinder having a formed adapter, load sensor and IR sensor.

The infrared ("IR") sensor 115 is included to detect the temperature of the reference material cylinder 40 as it is being filled with gas. It is anticipated that the IR sensor 115 is electronically coupled to the electronics control board 80 and assists with ensuring that the reference material cylinder 40 is not overheating due to compression of the gas filling the reference material cylinder.

The load sensor 110 is placed under the formed adapter 120. The formed adapter 120 fluidly couples the sealed ampule tube 5 to the reference material cylinder 40. The formed adaptor 120 includes a fulcrum point protrusion 122 for positioning above the load sensor 110. As gas is added to the reference material cylinder 40, the fulcrum point protrusion 122 moves down and contacts the load sensor 110 to measure the mass of gas added to the reference material cylinder. The formed adapter 120 is held in place by the second lid 52, thereby causing the reference material cylinder 40 to pull down as a cantilevered weight at the fulcrum point protrusion 122. Accordingly, an accurate weight can be observed as the reference material cylinder 40 is filled. In other embodiments, the fulcrum protrusion 122 may also be utilized with load sensor 110, although not shown in the drawing figures.

The use of the formed adapter 120 and load sensor 110 in combination with the IR sensor 115 avoids having to provide a weight sensor directly on each reference material cylinder 40 placed into the gas standard preparation device.

Prior to creating a Reference Material with the preparation station 50, the second lid 52 is lifted, the reference material cylinder 40 is placed in the fourth compartment, the first lid 51 is lifted, and the sealed ampule tube 5 is installed in the preparation station. The sealed ampule tube 5 is installed by connecting the first end of the ampule sleeve 15 of sealed ampule tube 5 to the second end of the gas/vacuum supply line 66 and joining the second end of the ampule sleeve 15 of sealed ampule tube 5 to the formed adaptor 120 of reference material cylinder 40. A vacuum pump 55 is fluidly coupled to the vacuum pump valve 56 and a diluent gas cylinder 60 filled with diluent gas is fluidly coupled to the diluent gas valve 61. The vacuum pump 55 is used to evacuate (remove any room air from) the tubes and sealed ampule tube 5 within the preparation station 50 and a leak check is performed. Once the room air is removed, the shutoff valve 42 of the reference material cylinder 40 is opened and a trickle flow of the diluent gas from the diluent gas cylinder 60 is released into the preparation station 50. Accordingly, the first lid 51 is closed, thereby breaking the ampule 10 and releasing the ampule reference material within the ampule 10 into the ampule sleeve 15. A preparation program is then started.

The preparation program is comprised of: (1) Heating the mandrel 70 to a desired temperature up to 240 degrees Celsius; (2) Flowing the diluent gas through the ampule sleeve 15 containing the broken ampule 10 to mix the diluent gas with the ampule reference material as they flow into the reference material cylinder; (3) Monitoring temperature on the reference material cylinder 40; (4) Pressurizing the cylinder to a final predetermined pressure; and (4) Closing the shutoff valve 42.

Once the preparation program is complete, then the concentration of the final reference material within the reference material cylinder 40 may be verified.

Second Embodiment

Figure 5:
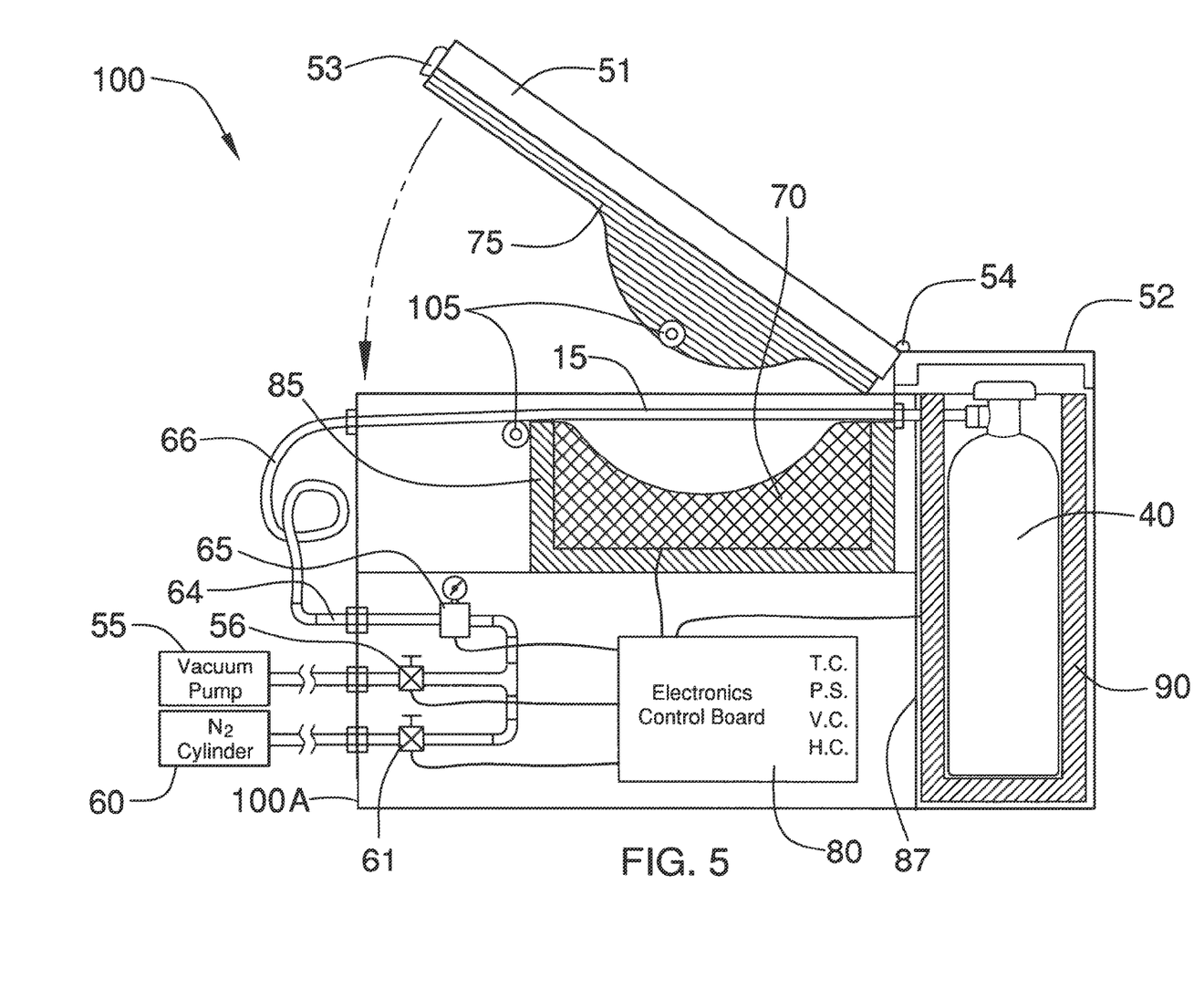
FIG. 5 shows a second non-limiting embodiment of the preparation station with the first lid in an open position.
Figure 6:
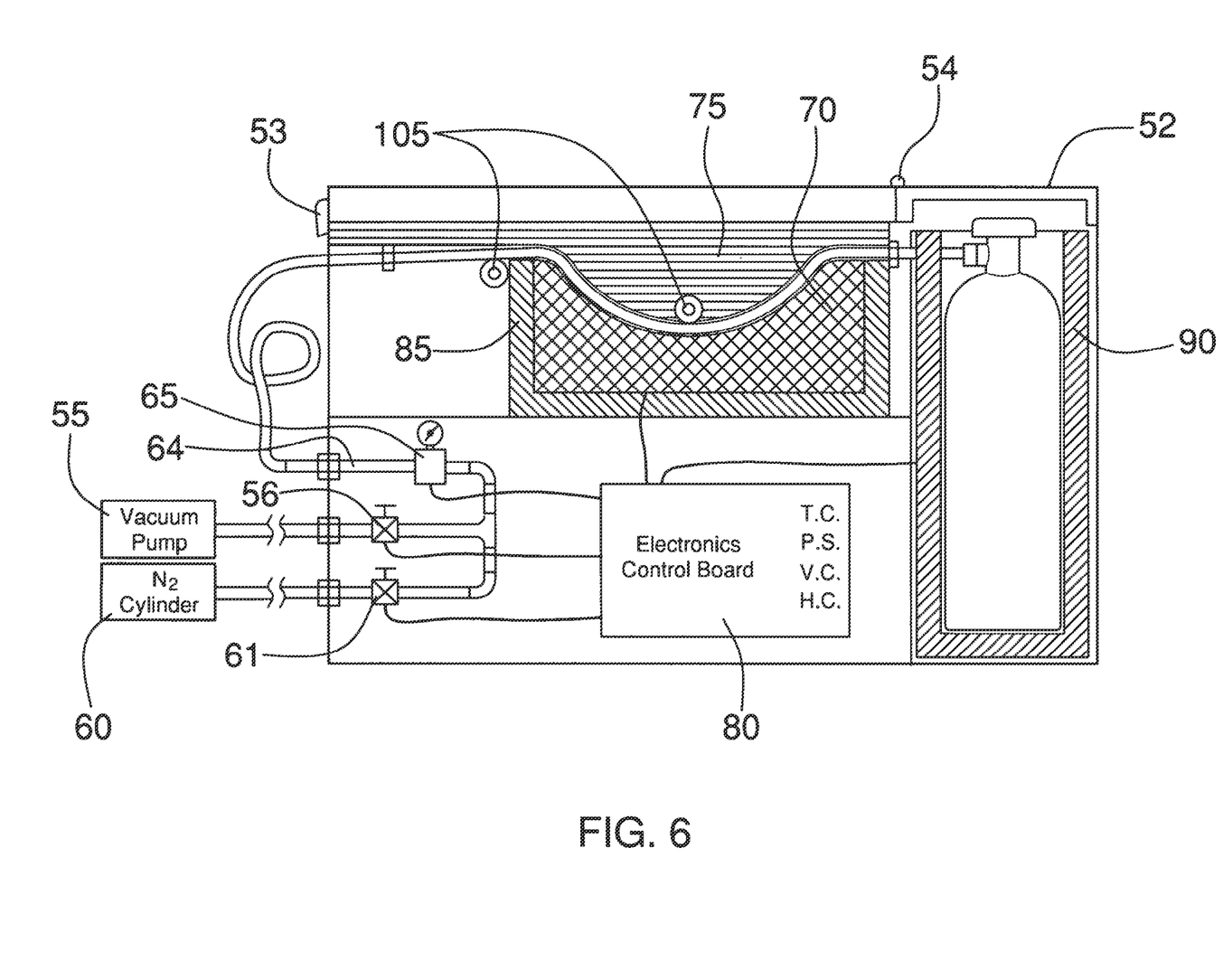
FIG. 6 shows the second non-limiting embodiment of the preparation station with the first lid in a closed position.

The second non-limiting embodiment for a preparation station 100 shares many components of the first embodiment for a preparation station 50, however this second embodiment for a preparation station 100 additionally utilizes a plurality of bearings 105. At least one bearing of the plurality of bearings 105 is placed on the lid mandrel 75 and at least one bearing of the plurality of bearings 105 is placed proximate to the heated mandrel 70, which is shown in FIG. 5 and FIG. 6. The second embodiment for a preparation station 100 also comprises a housing 100A and anticipates providing the gas/vacuum supply line 66 on the exterior of the housing.

Third Embodiment

Figure 8:
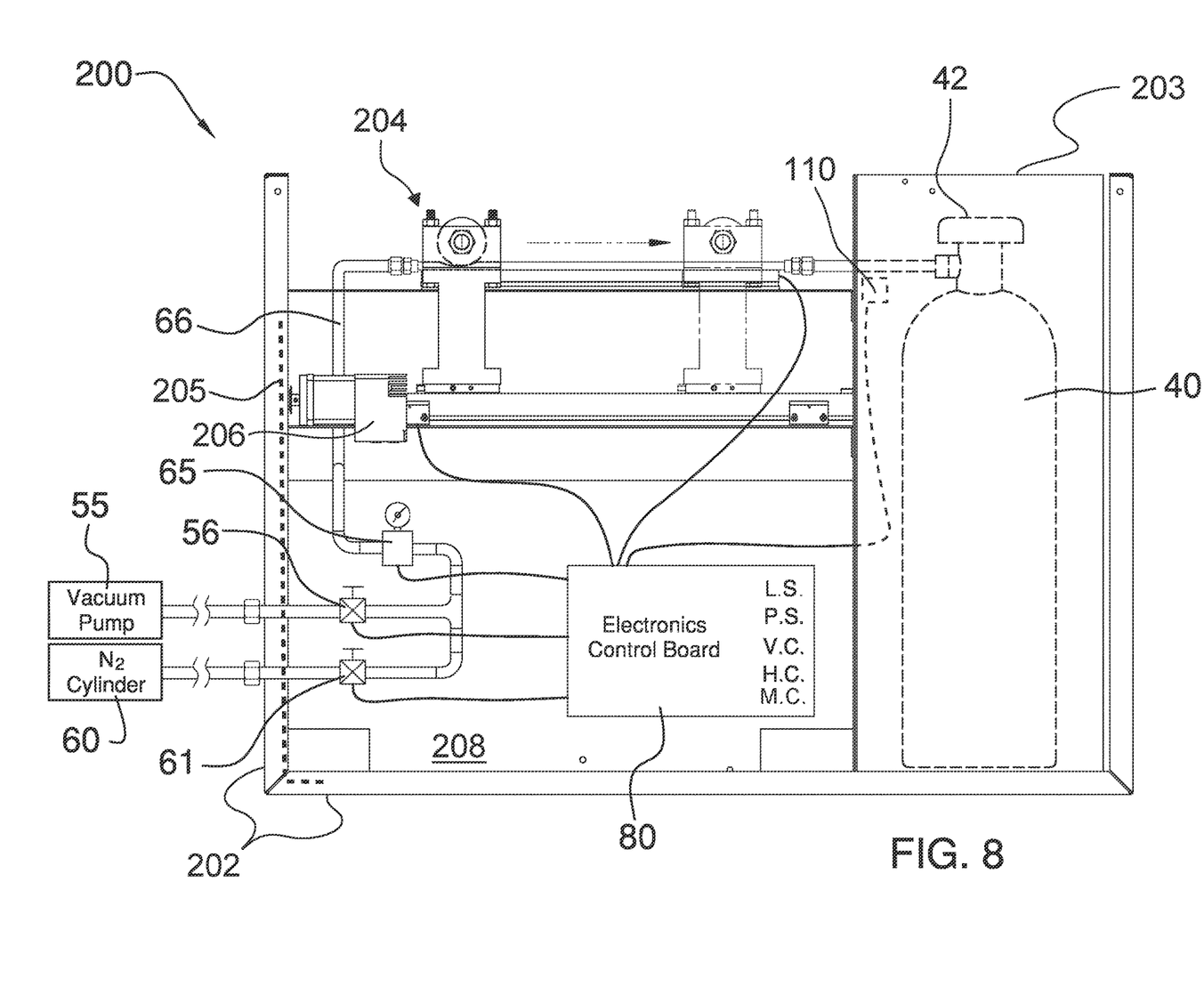
FIG. 8 shows a side elevation view of a third non-limiting embodiment of the preparation station.
Figure 9:
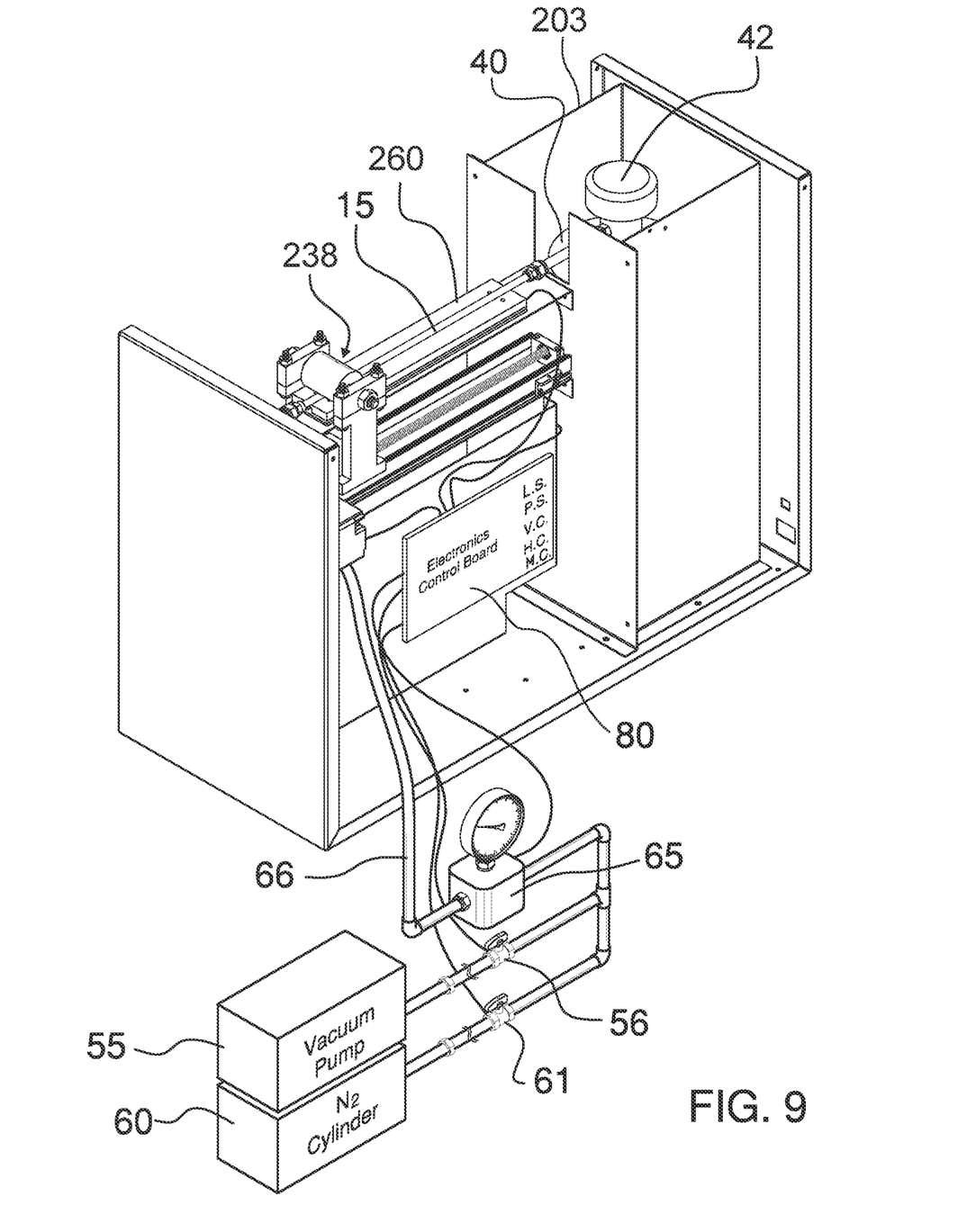
FIG. 9 shows a side elevation perspective view of the preparation station of FIG. 8.

The third non-limiting embodiment for a preparation station 200 shares many components of the first embodiment for a preparation station 50, which are disposed within or adjacent to a housing frame 202, as shown in FIGS. 8 and 9. Instead of four compartments, the preparation station 200 includes at least a separate metal shroud compartment 203 for containment of the reference material cylinder 40. Shroud compartment 203 includes one or more walls configured to surround at least the sides of the reference material cylinder 40. The shroud compartment 203 also houses the shutoff valve 42 and may include the load sensor 110. The preparation station 200 includes the housing frame 202, the shroud compartment 203, the sealed ampule tube 5, the gas/vacuum supply line 66 connected to the first end of the sealed ampule tube, the pressure sensor 65, the vacuum pump valve 56, the diluent gas valve 61, a crusher assembly 204, and the electronics control board 80.

Figure 10:
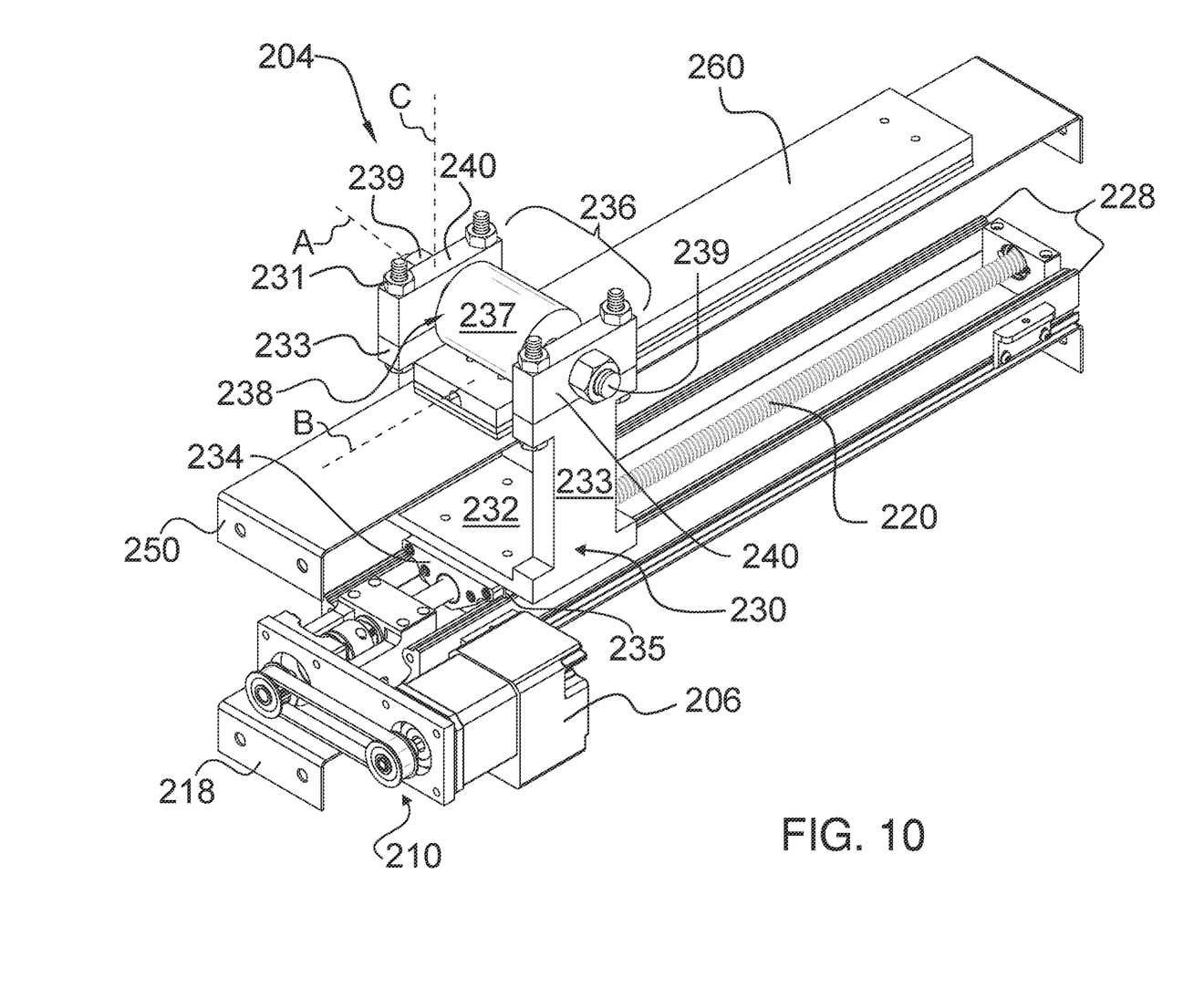
FIG. 10 shows a side elevation perspective view of the crusher assembly of the preparation station of FIG. 8.

The preparation station 200 utilizes the crusher assembly 204 to provide a uniform deformation of the ampule sleeve 15, thereby causing a controlled uniform load to be imparted to and thereby result in a breaching of ampule 10. Such breaching may include breaking of portions and/or crushing of portions of ampule 10, or breaking the ampule to the extent that it is breached. In this embodiment, the breaching may occur along the entire length of ampule 10. Such breaching of ampule 10 causes a substantially complete release of the ampule reference material within it, and dispersion of the ampule reference material into the ampule sleeve 15. Such a substantially complete release of the ampule reference material into the ampule sleeve 15 promotes a more thorough and complete blending with the diluent gas, once introduced. As shown in FIG. 10, the crusher assembly 204 includes a motor 206, a drive assembly 210, a lower support bracket 218, a screw shaft 220, a pair of opposing guide tracks 228, a carriage 230, an upper support bracket 250 and a mandrel base 260.

Figure 11:
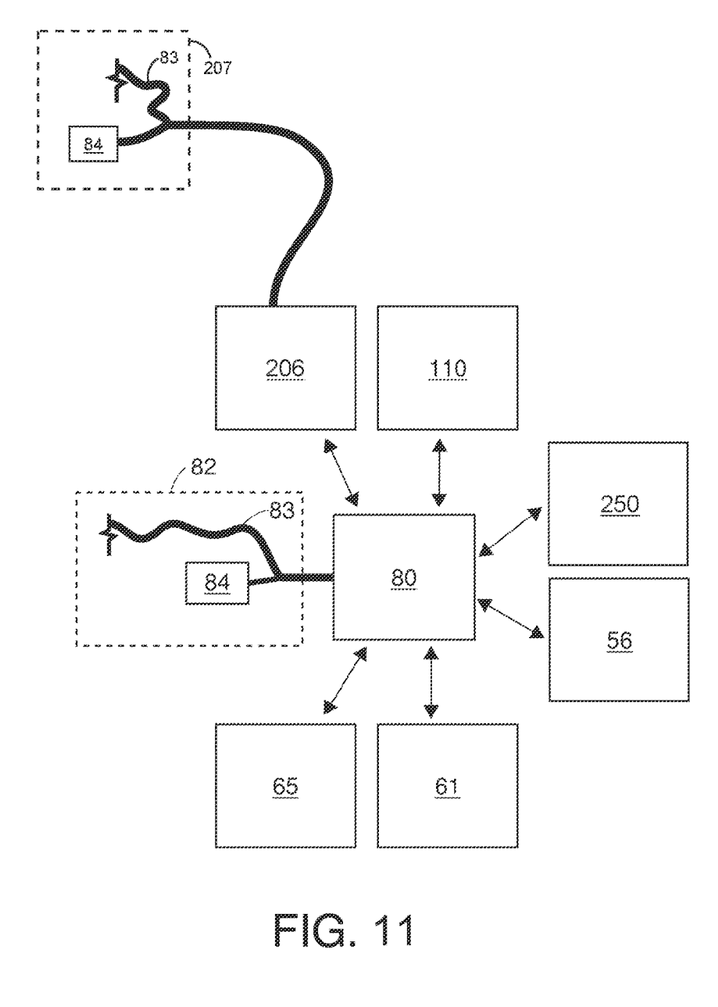
FIG. 11 is a schematic diagram of the electric/electronic components of the preparation station of FIG. 8.

As shown in FIGS. 8, 9 and 11, (similar to the first embodiment), the electronics control board 80 is configured to control the pressure sensor 65, the vacuum pump valve 56, the diluent gas valve 61, and the heater control (H.C.) which is connected to the mandrel base 260. In addition, it is anticipated that the mandrel base 260 includes heating elements and is electronically coupled to the electronics control board 80, as shown in FIG. 9. The heating elements would be configured to heat the mandrel base to a temperature of up to about 240 degrees maximum. The desired temperature would depend on what is needed for each application, which would depend on the compounds/chemicals contained within the ampule 10. The electronics control board 80 may also be electronically coupled with the optional load sensor 110 (L.S., see FIGS. 8 and 9) for monitoring the weight of the reference material cylinder 40 while it is being filled with gas, to determine the mass of gas being added (mass of gas added is used to determine total mass of gas to be used in calculating the final concentration). The electronics control board 80 is also electronically coupled with the motor 206 for motor control (M.C., see FIGS. 8 and 9) operations. As such, the electronics control board 80 is electronically coupled with the crusher assembly 204 for H.C. and M.C. Motor control operations may include, without limitation, energizing on/off, speed and direction of rotation of one or more components of the crusher assembly 204. The motor 206 is coupled to a motor power source 207, such as AC (alternating current) mains 83 or a battery 84.

The motor 206 is connected to the drive assembly 210, which is connected to the screw shaft 220 to provide linear movement of the carriage 230. Although a pully and belt type transmission is shown for the drive assembly 210, it may alternatively include gears, chains or other types of transmissions. In other aspects, the motor 206 may be configured for directly driving the screw shaft 220.

A support brace 205 is mounted on the vertical interior of the housing frame 202 and is configured to provide support for an electronics support wall 208, the lower support bracket 218, and the upper support bracket 250. The electronics support wall 208 provides mounting for at least the electronic control board 80 and is preferably connected to one of its sides, the support brace 205 and on at least one of its other sides is connected to the shroud compartment 203. The electronic support wall 208 may also be connected at its bottom side to the housing frame 202. The lower support bracket 218 is connected on one side to the support brace 205 and at the other side to the shroud compartment 203, and provides connection support for the drive assembly 210 and the pair of opposing guide tracks 228. The upper support bracket 250 is connected on one side to the support brace 205 and at the other side to the shroud compartment 203, and provides connection and support for the mandrel base 260.

The carriage 230 includes a U-brace 232, a nut bracket 234, a clamping assembly 236 and a crusher wheel assembly 238. The U-brace 232 includes a pair of opposing support arms 233, which are removably connected at the top end to the clamping assembly 236. A pair of opposing slides 235 mounted to the underside of the U-brace 232 are configured to slidably engage with the pair of opposing guide tracks 228. The nut bracket 234 is mounted on the bottom of the U-brace 232 and is configured to threadedly engage with the screw shaft 220.

In operation, the rotational motion provided by the motor 206 is transmitted via the drive assembly 210 to the screw shaft 220, and the rotation of the screw shaft advances the nut bracket 234 axially from end to end of the screw shaft and back, depending on the direction of rotation provided by the motor 206. As the nut bracket 234 axially advances, the U-brace 232 and the crusher wheel assembly 238 are also advanced linearly along a longitudinal central ampule mounting axis B of the mandrel base 260. The linear movement of the U-brace 232 is stabilized by slides 235 engaging the guide tracks 228.

The clamping assembly 236 includes a pair of opposing clamp brackets 240 and one or more fasteners 231. Although four screw bolt and nut type fasteners 231 are shown in the figures (installed via manual tightening), in other aspects, alternative fasteners may be utilizing, such as one or more cam clamping members having actuation levers. In other aspects, alternative clamping members may be utilized whereby a single lever, handle or other means of actuation is used to securely clamp the clamp brackets 240 of the clamping assembly 236 to the opposing support arms 233.

The crusher wheel assembly 238 includes a crusher wheel 237 removably connected in-between the pair of opposing clamp brackets 240 via a pair of opposing wheel mountings 239. The crusher wheel 237 is coaxially connected at each end to one of each of the opposing wheel mountings 239, which allows for removable connection to the clamping assembly 236. The crusher wheel assembly 238 is configured such that the longitudinal central axis A of the crusher wheel 237 is mounted substantially perpendicular to the vertical axis C of the support arms 233 and mounted substantially perpendicular to the longitudinal central ampule mounting axis B of the mandrel base 260.

In operation, the reference material cylinder 40 is placed within housing frame 202. The U-brace 232 is set in its predetermined initial horizontal starting position relative to the screw shaft 220. The sealed ampule tube 5 is installed in a predetermined position along the longitudinal central ampule mounting axis B, proximate to the mandrel base 260. The sealed ampule tube 5 is installed by connecting the first end of the ampule sleeve 15 of the sealed ampule tube 5 to the second end of the gas/vacuum supply line 66 and connecting the second end of the ampule sleeve 15 of the sealed ampule tube 5 to the formed adaptor 120 of the reference material cylinder 40. The vacuum pump 55 is fluidly coupled to the vacuum pump valve 56 and the diluent gas cylinder 60 filled with diluent gas is fluidly coupled to the diluent gas valve 61. The vacuum pump 55 is used to evacuate (remove any room air from) the tubes and the sealed ampule tube 5 within the preparation station and a leak check is performed. Once the room air is removed, the shutoff valve 42 of the reference material cylinder 40 is opened and a trickle flow of the diluent gas from the diluent gas cylinder 60 is released into the sealed ampule tube 5.

The clamping assembly 236 is then positioned against the opposing support arms 233 and installed to be securely clamped to the support arms via the one or more fasteners 231. The clamping assembly 236 is securely clamped to the opposing support arms 233 such that there is substantially zero clearance in-between the bottom of the clamp brackets 240 and the top of the support arms 233. As the clamping assembly 236 is being clamped down, the bottom of the crusher wheel 237 deforms the top of the ampule sleeve 15 to a predetermined depth at the initial horizontal starting position. Next, the motor 206 is energized and controlled to begin the forward linear advancement of the crusher wheel 237 from the initial horizontal starting position to a predetermined finishing position relative to the screw shaft 220 as required to breach ampule 10. Once the crusher wheel 237 reaches the ampule 10, it begins to breach ampule 10, to release the ampule reference material into the ampule sleeve 15. Next, a preparation program is then started.

The preparation program is comprised of: (1) Heating the mandrel base 260 to a desired temperature up to 240 degrees Celsius; (2) Flowing the diluent gas through the ampule sleeve 15 containing the broken ampule 10 to mix the diluent gas with the ampule reference material as they flow into the reference material cylinder 40; (3) pressurizing the cylinder to a final predetermined pressure; and (4) Closing the shutoff valve 42.

In this embodiment, it is anticipated during step (3) of the preparation program, the mass of the gas being added to reference material cylinder 40 is determined by the gas pressure, which can be monitored at the pressure sensor 65. Once the preparation program is complete, an external balance type scale may be used to verify the weight of reference material cylinder 40.

Once reaching the finishing position, motor 206 is controlled to reverse direction and return crusher wheel 237 to the initial starting position. Crusher wheel 237 is controlled to be moving its course forward and then reverse against ampule sleeve 15 while the mixture of ampule reference material and diluent gas flow into the reference material cylinder 40. Once the crusher wheel 237 returns to the initial starting position by moving over the ampule 10 for a second time, then the motor 206 is deenergized and controlled to end the linear advancement of the crusher wheel. At this point, the clamping assembly 236 may be removed from the opposing support arms 233, thus removing the crusher wheel 237 from engagement with the ampule sleeve 15.

Once the preparation program is complete, then the concentration of the final reference material within the reference material cylinder 40 may be verified. The user may further certify the final reference material onsite, or alternatively, send it out for independent certification. The International Organization for Standardization (ISO) guidelines provide standardization requirements for certified reference materials and reference materials, such ISO 17034 and ISO/IEC 17025, for example.

While the embodiments of the one or more non-limiting embodiments have been disclosed, certain modifications may be made by those skilled in the art to modify the embodiments without departing from the scope of the claims.

The inventor claims:

1. A gas phase standard preparation device comprising:
   a. a housing frame;
   b. a sealed ampule tube;
      wherein the sealed ampule tube is further comprised of an ampule, an ampule sleeve, a first connector and a second connector;
      wherein the ampule is provided within the ampule sleeve;
      wherein the ampule sleeve has a first end and a second end;
   c. a gas/vacuum supply line;
      wherein the gas/vacuum supply line has a first end and a second end;

wherein the second end of the gas/vacuum supply line is connected to the first end of the ampule sleeve;
d. a pressure sensor;
  wherein the pressure sensor is connected to the first end of the gas/vacuum supply line;
e. a vacuum pump valve;
  wherein the vacuum pump valve is fluidly coupled to the pressure sensor;
f. a diluent gas valve;
  wherein the diluent gas valve is fluidly coupled to the pressure sensor;
g. a crusher assembly;
  wherein the crusher assembly is configured to provide a uniform deformation of the ampule sleeve, thereby causing a breaching of the ampule; and
h. an electronics control board;
  wherein the electronics control board electronically couples to the crusher assembly, the pressure sensor, the vacuum pump valve, and the diluent gas valve.

2. The gas phase standard preparation device of claim 1 wherein the sealed ampule tube is removable.

3. The gas phase standard preparation device of claim 1 wherein a reference material cylinder is connected to the second end of the ampule sleeve.

4. The gas phase standard preparation device of claim 3 further comprising a formed adaptor having a first end and a second end, wherein the second end of the ampule sleeve is connected to the first end of the formed adaptor, and the second end of the formed adaptor is connected to the reference material cylinder.

5. The gas phase standard preparation device of claim 4 further comprising a shroud compartment for containment of the reference material cylinder.

6. The gas phase standard preparation device of claim 5 further comprising a load sensor electronically coupled to the electronics control board to allow for monitoring the weight of the reference material cylinder to determine the mass of gas being added.

7. The gas phase standard preparation device of claim 6 wherein the formed adaptor further comprises a fulcrum point protrusion for positioning above the load sensor, wherein as gas is added to the reference material cylinder, the fulcrum point protrusion moves down and contacts the load sensor to measure the mass of gas added to the reference material cylinder.

8. The gas phase standard preparation device of claim 1 wherein the crusher assembly further comprises a motor, a drive assembly, a lower support bracket, a screw shaft, a pair of opposing guide tracks, a carriage, an upper support bracket and a mandrel base;
  wherein the motor is connected to the drive assembly, which is connected to the screw shaft to provide linear movement of the carriage.

9. The gas phase standard preparation device of claim 8 wherein the mandrel base includes heating elements.

10. The gas phase standard preparation device of claim 8 wherein the carriage includes a U-brace, a nut bracket, a clamping assembly and a crusher wheel assembly;
  wherein the nut bracket is mounted on the bottom of the U-brace and is configured to threadedly engage with the screw shaft.

11. The gas phase standard preparation device of claim 10 wherein the carriage further comprises a pair of opposing slides mounted to the underside of the U-brace and are configured to slidably engage with the pair of opposing guide tracks.

12. The gas phase standard preparation device of claim 11 wherein the U-brace includes a pair of opposing support arms, which are removably connected at a top end thereof to the clamping assembly.

13. The gas phase standard preparation device of claim 12 wherein the clamping assembly includes a pair of opposing clamp brackets and one or more fasteners.

14. The gas phase standard preparation device of claim 13 wherein the crusher wheel assembly includes a crusher wheel removably connected in-between the pair of opposing clamp brackets via a pair of opposing wheel mountings.

15. The gas phase standard preparation device of claim 14 wherein the crusher wheel is coaxially connected at each end to one of each of the opposing wheel mountings which allows for removable connection to the clamping assembly.

16. The gas phase standard preparation device of claim 15 wherein the crusher wheel assembly is configured such that a longitudinal central axis of the crusher wheel is mounted substantially perpendicular to a vertical axis of the support arms and mounted substantially perpendicular to a longitudinal central ampule mounting axis of the mandrel base.

17. A method of using the gas phase standard preparation device of claim 3 above comprising:
  obtaining the gas phase standard preparation device of claim 3, then;
  a. placing the reference material cylinder into the housing frame;
  b. connecting the first end of the ampule sleeve to the gas/vacuum supply line;
  c. connecting the second end of the ampule sleeve to the reference material cylinder;
  d. evacuating the ampule sleeve;
  e. leak-checking the ampule sleeve;
  f. opening a shutoff valve of the reference material cylinder;
  g. starting a trickle flow of a diluent gas into the gas phase standard preparation device;
  h. energizing a motor of the crusher assembly to provide linear movement of a carriage to provide a breaching of the ampule;
  i. breaching the ampule and releasing ampule reference material;
  j. starting a preparation program;
  k. filling the reference material cylinder with the diluent gas and the ampule reference material, thereby forming a final reference material; and
  l. closing the shutoff valve of the reference material cylinder.

18. The method of using the gas phase standard preparation device of claim 17 wherein the preparation program comprising:
  a. heating a mandrel base to a predetermined temperature;
  b. flowing diluent gas through the ampule sleeve containing the breached ampule; and
  c. pressurizing the reference material cylinder to a predetermined pressure.

19. The method of using the gas phase standard preparation device of claim 18 further comprising:
  heating the mandrel base to a desired temperature up to 240 degrees Celsius.

* * * * *

UNITED STATES PATENT AND TRADEMARK OFFICE
CERTIFICATE OF CORRECTION

Page 1 of 1

PATENT NO. : 12,392,696 B2
APPLICATION NO. : 17/839434
DATED : August 19, 2025
INVENTOR(S) : Doug Markle It is certified that error appears in the above-identified patent and that said Letters Patent is hereby corrected as shown below:

In the Claims

Claim 17, Lines 26-27, "of claim 3" should be deleted.

Signed and Sealed this
Fourteenth Day of October, 2025

John A. Squires
*Director of the United States Patent and Trademark Office*